United States Patent [19]

Diehr

[11] Patent Number: 5,026,864
[45] Date of Patent: Jun. 25, 1991

[54] PREPARATION OF 2-CHLORO-5-AMINOMETHYL-PYRIDINE

[75] Inventor: Hans-Joachim Diehr, Wuppertal, Fed. Rep. of Germany

[73] Assignee: Bayer Aktiengesellschaft, Leverkusen, Fed. Rep. of Germany

[21] Appl. No.: 502,604

[22] Filed: Mar. 30, 1990

[30] Foreign Application Priority Data

Apr. 7, 1989 [DE] Fed. Rep. of Germany ....... 3911224

[51] Int. Cl.$^5$ .................. C07D 213/26; C07D 213/36
[52] U.S. Cl. .................................... 546/345; 546/346
[58] Field of Search .......................................... 546/345

[56] References Cited

U.S. PATENT DOCUMENTS 4,499,097 2/1989 Tomcufcik et al. ................ 514/341

FOREIGN PATENT DOCUMENTS 3726993 2/1989 Fed. Rep. of Germany ...... 546/345
3727126 2/1989 Fed. Rep. of Germany ...... 546/345

Primary Examiner—Alan L. Rotman
Attorney, Agent, or Firm—Sprung Horn Kramer & Woods

[57] ABSTRACT

A process for the preparation of 2-chloro-5-aminomethyl-pyridine of the formula

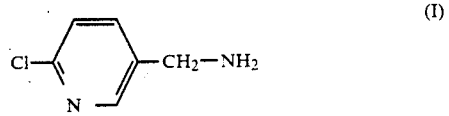

(I)

comprising reacting 2-chloro-5-chloromethyl-pyridine of the formula

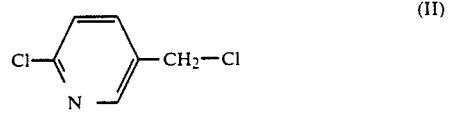

(II)

with excess ammonia, optionally in the presence of a diluent, at a temperature between about −50° C. and +50° C.

9 Claims, No Drawings

PREPARATION OF 2-CHLORO-5-AMINOMETHYL-PYRIDINE

The invention relates to a new process for the preparation of the known 2-chloro-5-aminomethyl-pyridine.

It is known that 2-chloro-5-aminomethyl-pyridine, an intermediate for the preparation of insecticides, is obtained when, in a first step, 2-chloro-5-chloromethyl-pyridine is reacted with phthalimide in the presence of potassium hydroxide, dimethylformamide and ethanol to give N-(2-chloro-pyridin-5-yl-methyl)-phthalimide and, in a second step, the desired 2-chloro-5-aminomethyl-pyridine is liberated from this using hydrazine hydrate in ethanol (cf. EP-A 302,389, p. 23).

Furthermore, 2-chloro-5-aminomethyl-pyridine is known as an intermediate for the preparation of hypotensive agents (cf. U.S. Pat. No. 4,499,097).

A hitherto still unsatisfied need thus existed for a simpler, if possible one-step, preparation process for 2-chloro-aminomethyl-pyridine starting from 2-chloro-5-chloromethyl-pyridine.

A process for the preparation of 2-chloro-5-aminomethyl-pyridine of the formula (I)

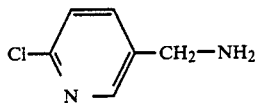

has been found, which is characterized in that 2-chloro-5-chloromethyl-pyridine of the formula (II)

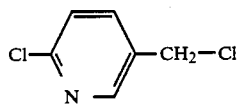

is reacted with excess ammonia, if appropriate in the presence of a diluent, at temperatures between −50° C. and +50° C.

It must be regarded as surprising that the process according to the invention leads to the product of the formula (I) in high selectivity, since a nucleophilic displacement of the second chlorine substituent also had to be expected.

Advantages of the new process lie in the fact that it is simple to carry out and in the good yield and high quality of the product.

The course of the reaction in the process according to the invention can be represented by the following equation:

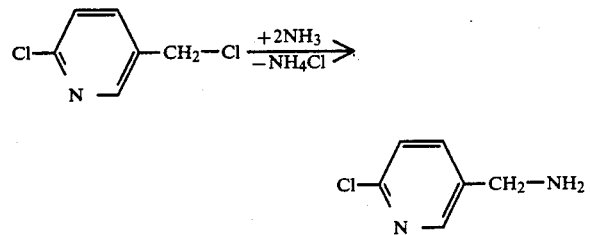

The 2-chloro-5-chloromethyl-pyridine of the formula (II) to be used as a starting substance in the process according to the invention is already known (cf. U.S. Pat. No. 4,332,944; J. Heterocycl. Chem. 16 (1979), 333–337).

The process according to the invention is preferably carried out using a diluent. Possible diluents in this case are virtually all inert organic solvents. These preferably include aliphatic and aromatic, optionally halogenated hydrocarbons, such as hexane, heptane, octane, cyclohexane, methylcyclohexane, benzene, toluene, xylene, chlorobenzene and o-dichlorobenzene, and ethers such as diethyl ether, dipropyl ether, diisopropyl ether, dibutyl ether, diisobutyl ether, tetrahydrofuran, dioxane, glycol dimethyl ether and diglycol dimethyl ether.

Toluene is very particularly preferred as a diluent.

The reaction temperatures can be varied within a relatively wide range in the process according to the invention. In general, the process is carried out at temperatures between −50° C. and +50° C., preferably at temperatures between −35° C. and +25° C.

The process according to the invention is in general carried out at normal pressure or under an elevated pressure of up to about 20 bar, preferably up to 10 bar.

In order to carry out the process according to the invention, between 100 ml and 2000 ml, preferably between 300 ml and 1500 ml, of ammonia (liquid) are in general employed per mol of 2-chloro-5-chloromethyl-pyridine of the formula (II).

In order to carry out the process according to the invention, the 2-chloro-5-chloromethyl-pyridine, the ammonia and the diluent can be added together in any sequence.

In a preferred embodiment of the process according to the invention, the ammonia (liquid) is initially introduced into an autoclave and the 2-chloro-5-chloromethyl-pyridine is slowly metered in, preferably dissolved or suspended in a suitable diluent. The reaction mixture is stirred until the reaction is complete and is then worked up by customary methods (compare Preparation Example).

PREPARATION EXAMPLE

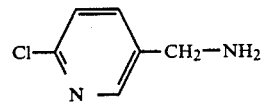

N 1 l of ammonia (liquid) is initially introduced into an autoclave and a solution of 176 g (92% pure, 1 mol) of 2-chloro-5-chloromethyl-pyridine in 0.5 l of toluene, which has been cooled to 0° C. to 5° C., is metered in in the course of about 20 minutes using a pump (maximum pressure in the autoclave about 10 bar). The reaction mixture is stirred at 0° C. to 5° C. for 8 hours and, after depressurizing, added to a mixture of 250 ml of 45% strength aqueous sodium hydroxide solution and 500 ml of toluene.

The organic phase is separated off after shaking thoroughly, the aqueous phase is shaken once more with toluene and the organic phases are then combined. After concentrating in a water jet vacuum, the residue which remains (146 g) is distilled in vacuo at 3–4 mbar.

102 g (purity by GC 87.3%, yield: 70% of theory) of 2-chloro-5-aminomethyl-pyridine of boiling range 112° C.–114° C. (3–4 mbar) are obtained.

It is understood that the specification and examples are illustrative but not limitative of the present inven-

I claim:

1. A process for the preparation of 2-chloro-5-aminomethy-pyridine of the formula

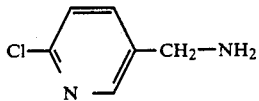   (I)

comprising reacting 2-chloro-5-chloromethyl-pyridine of the formula

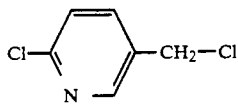   (II)

with excess ammonia, optionally in the presence of a diluent, at a temperature between about −50° C. and +50° C.

2. A process according to claim 1, wherein the reaction is carried out in the presence of an inert organic solvent.

3. A process according to claim 1, wherein the reaction is carried out in the presence of toluene.

4. A process according to claim 1, wherein the reaction is carried out at a temperature between about −35° C. and +25° C.

5. A process according to claim 1, wherein the reaction is carried out under normal pressure.

6. A process according to claim 1, wherein the reaction is carried out at an elevated pressure of up to about 20 bar.

7. A process according to claim 1, wherein about 100 to 2000 ml of liquid ammonia are employed per mol of 2-chloro-5-chloromethyl-pyridine.

8. A process according to claim 1, wherein about 300 and 1500 ml of liquid ammonia are employed per mol of 2-chloro-5-chloromethyl-pyridine.

9. A process according to claim 8, wherein the reaction is carried out in the presence of toluene at a temperature between about −35° C. and +25° C. under a pressure from normal up to about 20 bar.

* * * * *